(12) United States Patent
Neusch (10) Patent No.: US 10,227,742 B2
(45) Date of Patent: Mar. 12, 2019

(54) ANTI-RAM SLIDING CRASH GATE

(71) Applicant: NEUSCH INNOVATIONS, LP, Marble Falls, TX (US)

(72) Inventor: William H. Neusch, Marble Falls, TX (US)

(73) Assignee: NEUSCH INNOVATIONS, LP, Marble Falls, TX (US)

( * ) Notice: Subject to any disclaimer, the term of this patent is extended or adjusted under 35 U.S.C. 154(b) by 69 days.

(21) Appl. No.: 15/172,141

(22) Filed: Jun. 2, 2016

(65) Prior Publication Data

US 2016/0356006 A1 Dec. 8, 2016

Related U.S. Application Data

(60) Provisional application No. 62/171,948, filed on Jun. 5, 2015.

(51) Int. Cl.
| | |
|---|---|
| *E01F 13/00* | (2006.01) |
| *E01F 13/04* | (2006.01) |
| *E01F 13/12* | (2006.01) |
| *E06B 11/04* | (2006.01) |
| *E06B 11/02* | (2006.01) |

(52) U.S. Cl.
CPC ............ *E01F 13/048* (2013.01); *E01F 13/12* (2013.01); *E06B 11/045* (2013.01); *E06B 11/026* (2013.01)

(58) Field of Classification Search
CPC ....... E01F 13/048; E01F 13/12; E06B 11/045; E06B 11/026
USPC .............................. 49/49, 404, 360; 404/6, 9
See application file for complete search history.

(56) References Cited

U.S. PATENT DOCUMENTS

| | | | | |
|---|---|---|---|---|
| 923,884 | A | | 6/1909 | Pickett |
| 1,277,844 | A | | 9/1918 | Browne |
| 2,543,893 | A | * | 3/1951 | Chandler ............... E06B 11/02 49/131 |
| 4,858,383 | A | * | 8/1989 | Kendig ................. E05F 15/635 256/1 |
| 5,509,754 | A | * | 4/1996 | Conigliaro ............ E01F 13/048 404/9 |

(Continued)

FOREIGN PATENT DOCUMENTS

| | | | |
|---|---|---|---|
| DE | 3619516 A1 | * 12/1987 | ......... E05D 15/0617 |
| JP | 04319193 A | * 11/1992 | |
| WO | 2012095650 A2 | 7/2012 | |

OTHER PUBLICATIONS

International Search Report and Written Opinion, PCT/US16/35603, dated Oct. 5, 2016.

(Continued)

*Primary Examiner* — Jerry E Redman
(74) *Attorney, Agent, or Firm* — Winstead PC (57) ABSTRACT

A crash gate assembly includes a buttress post assembly secured in the ground and having two vertical buttress posts forming a barrier passage, a latch post assembly secured in the ground on the opposite side of a roadway from the buttress post assembly, the latch post assembly including two vertical latch posts forming a gap, and a barrier including a horizontal gate beam disposed in the barrier passage and extending from a buttress end to a latch end, the barrier slidingly positioned in a closed position with the barrier extending across the roadway and the latch end disposed in the latch gap.

20 Claims, 6 Drawing Sheets

(56) References Cited

U.S. PATENT DOCUMENTS

| | | | | |
|---|---|---|---|---|
| 5,520,479 A * | 5/1996 | Hernandez | ............ | E01F 13/026 256/13.1 |
| 5,711,110 A * | 1/1998 | Williams | ............. | E01F 13/085 49/25 |
| 5,829,912 A | 11/1998 | Marcotullio et al. | | |
| 5,847,316 A * | 12/1998 | Takada | ................ | H05K 9/0001 174/374 |
| 6,796,084 B2 * | 9/2004 | Gagnon | ................. | E01F 13/06 49/226 |
| 7,121,041 B2 | 10/2006 | Anderson et al. | | |
| 7,641,416 B2 * | 1/2010 | Miracle | ................ | E01F 13/044 404/6 |
| 7,818,920 B2 * | 10/2010 | Causey | .................. | E01F 13/06 49/49 |
| 7,946,086 B2 * | 5/2011 | Hammer | ................... | E04C 5/08 52/223.5 |
| 8,176,684 B2 * | 5/2012 | Marchetto | ........ | G07C 9/00182 49/360 |
| 8,534,005 B2 | 9/2013 | Thomas et al. | | |
| 2003/0233798 A1 * | 12/2003 | Berkey | ................... | E02D 27/02 52/223.7 |
| 2006/0288643 A1 * | 12/2006 | Henshell | ................ | E01F 13/06 49/49 |
| 2008/0226391 A1 * | 9/2008 | Phillips | ................. | E01F 13/048 404/6 |
| 2010/0024307 A1 * | 2/2010 | Dale | ..................... | E01F 13/048 49/360 |
| 2011/0062403 A1 | 3/2011 | Neusch | | |

OTHER PUBLICATIONS

"Frontier Pits Terra G8 Sliding Cantilevered Gate crash test." FrontierPitts. Dec. 19, 2014, retrieved from www.youtube on Sep. 8, 2016.

"Legate Invisible Grille (New Product Luanch 2014)—Cantilever." Legate Invisible Grille. Retrieved from www.youtube on Sep. 8, 2016.

"Foundation Plan." Inova. Retrieved from www.youtube on Sep. 8, 2016.

* cited by examiner

ANTI-RAM SLIDING CRASH GATE

CROSS-REFERENCES TO RELATED APPLICATIONS

This application claims the benefit under 35 U.S.C. § 119(e) of U.S. Provisional Patent Application No. 62/171,948 filed Jun. 5, 2015, which is incorporated herein by reference in its entirety as if fully set forth herein.

BACKGROUND

This section provides background information to facilitate a better understanding of the various aspects of the disclosure. It should be understood that the statements in this section of this document are to be read in this light, and not as admissions of prior art.

Vehicle barrier systems are utilized to guard against access to protected areas. In particular, the systems are provided to stop motor vehicles, such as trucks, from being intentionally driven into certain areas for nefarious purposes. At least one agency of the United States Government has provided standards to certify barriers for use.

SUMMARY

A crash gate assembly includes a buttress post assembly secured in the ground and having two vertical buttress posts forming a barrier passage, a latch post assembly secured in the ground on the opposite side of a roadway from the buttress post assembly, the latch post assembly including two vertical latch posts forming a gap, and a barrier including a horizontal gate beam disposed in the barrier passage and extending from a buttress end to a latch end, the barrier slidingly positioned in a closed position with the barrier extending across the roadway and the latch end disposed in the latch gap.

A method of mounting a crash gate assembly includes providing a barrier comprising a rectangular frame including a horizontal gate beam extending from a buttress end to a latch end, securing a buttress post assembly and a latch post assembly on opposite sides of a roadway, the buttress post assembly having two vertical buttress posts forming a barrier passage and the latch post assembly having two vertical latch posts forming a gap, and mounting the barrier in the barrier passage and on a sliding mechanism between the buttress post assembly and the latch post assembly, in a closed position the barrier extending across the roadway with the latch end positioned in the latch gap.

This summary is provided to introduce a selection of concepts that are further described below in the detailed description. This summary is not intended to identify key or essential features of the claimed subject matter, nor is it intended to be used as an aid in limiting the scope of claimed subject matter.

BRIEF DESCRIPTION OF THE DRAWINGS

The disclosure is best understood from the following detailed description when read with the accompanying figures. It is emphasized that, in accordance with standard practice in the industry, various features are not drawn to scale. In fact, the dimensions of various features may be arbitrarily increased or reduced for clarity of discussion.

DETAILED DESCRIPTION

It is to be understood that the following disclosure provides many different embodiments, or examples, for implementing different features of various embodiments. Specific examples of components and arrangements are described below to simplify the disclosure. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed.

Figure 1:
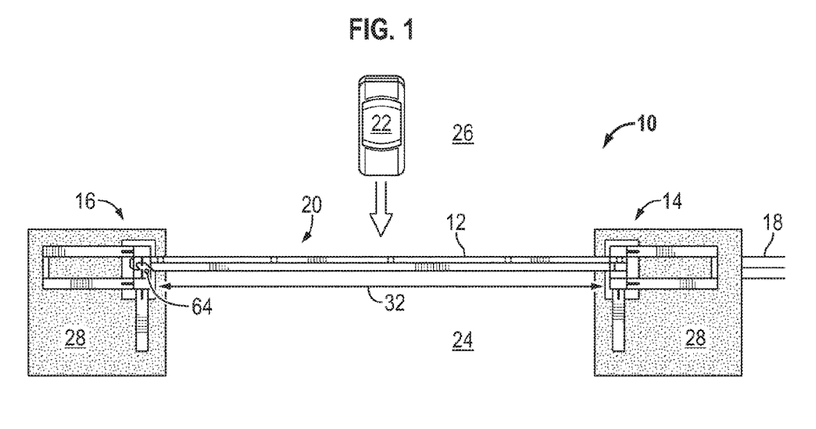
FIG. 1 is a plan view of an anti-ram sliding crash gate according to one or more aspects of the disclosure.
Figure 2:
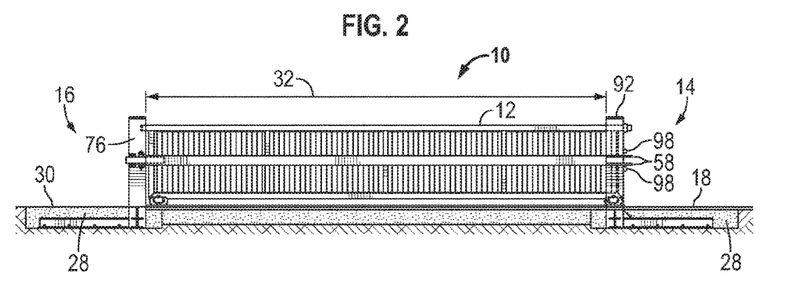
FIG. 2 is an elevation view of an anti-ram sliding crash gate according to one or more aspects of the disclosure.
Figure 3:
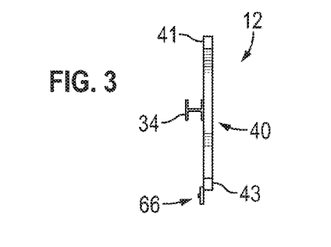
FIG. 3 is a side elevation view of an example of an anti-ram sliding crash gate according to one or more aspects of the disclosure.

FIGS. 1 and 2 illustrate an anti-ram crash gate assembly 10 according to one or more aspects of the disclosure, which is described with reference to FIGS. 1-16. Assembly 10 includes a barrier 12 (i.e., gate) in the closed position extending between a buttress post assembly 14 and a latch post assembly 16 positioned on opposite sides of a roadway 20 (e.g., paved or unpaved path for motor vehicles) also referred to as an entry port. The barrier 12 can be moved laterally to the right in FIGS. 1 and 2, for example along a track 18, to the open position permitting passage across the roadway 20 between the buttress and latch post assemblies. The track 18, if utilized, may extend to the latch post assembly 16.

In the closed position, the gate assembly 10 is an anti-ram crash barrier configured to stop the penetration of a motor vehicle 22 that crashes into the barrier 12. The barrier 12 should fully stop an impacting vehicle within a desired penetration distance. United States federal agencies (e.g., the U.S. Department of Defense (DOD) and the Department of State (DOS)) have developed test standards using crash tests to quantify, verify, and certify barrier performance. Such test methods were initially published by the U.S. Dept. of State in 1985 as SD-STD-02.01, which was revised in 2003 as SD-STD-02.01 Revision A, and which was replaced in 2009 with ASTM F2656-07 (Standard Test Method for Vehicle Crash Testing of Perimeter Barriers). Embodiments of the disclosed gate assembly 10 are configured to be crash-rated by certifying agencies such as DOD, DOS, ASTM and British Standards (BSI). Vehicle barriers are tested by crashing a motor vehicle from a perpendicular direction into the barrier. The vehicle barrier is rated based on the test vehicles weight, the speed of impact, and the penetration of the vehicle (e.g., the cargo bed) beyond the pre-impact inside edge of the barrier. For example, a "K" or "M" designates a medium duty vehicle with a gross-weight of 15,000 pounds (6810 kg). The speed ratings include K4/M30 for traveling at 28.0 to 37.9 miles per hour (mph), K8/M40 traveling at 38.0 to 46.9 mph, and K12/M50 traveling at 47.0 mph and above. The penetration ratings include P1 for less than or equal to 1 meter (3.3 ft.), P2 for 1.10 to 7 m (3.31 to 23.0 ft.), P3 for 7.01 to 30 m (23.1 to 98.4 ft.), and P4 for 30 m (98 ft.) or greater. For example, a M50 P1 crash barrier is designed to stop a medium duty truck traveling 50 mph with a penetration distance of 3.3 feet or less.

In FIG. 1 the gate assembly 10 is positioned between a protected side 24 and the motor vehicle 22 approaching from the attack side 26. In accordance with aspects of the disclosure the gate assembly 10 is configured to achieve a crash-rating. In some embodiments the gate assembly 10 is configured to achieve a crash-rating of M50 P1.

The buttress and latch post assemblies 14, 16 are each set in concrete foundations 28 extending below the grade line 30. The roadway 20 which is blocked by the barrier 12 extends a length 32 between the buttress and latch post assemblies. In the non-limiting examples illustrated in FIGS. 1 and 2, the length 32 is for example about 28 feet and the buttress and latch post assemblies are each set in concrete foundations 28 that are less than about two feet in depth (thickness) below the grade level 30. The foundations 28 may be shallow or deep foundations. A shallow foundation may be considered for example having a depth of about twenty inches or less. According to aspects of the system, the foundation 28 may be about eighteen inches or less. According to aspects of the system, the foundation 28 may be about twelve inches or less.

FIGS. 3 to 6 illustrate an example of a barrier 12 according to one or more aspects of the disclosure. In the illustrated example, barrier 12 is a substantially rectangular structure (i.e., frame 40) and includes a horizontal gate beam 34 extending from a buttress end 36 to a latch end 38 and located proximate to the center of the gate frame 40. In a non-limiting example, the gate beam is a wide flange beam, for example a W6×25 beam (i.e., 6 inches deep with a weight of 25 lbs/ft.). Gate frame 40 is defined along the top and bottom sides by top and bottom horizontal members 41, 43 and on the vertical sides by first and second vertical members 42, 44. As illustrated for example in FIG. 4 the top horizontal member 41 is longer than the bottom horizontal member 43. The first and second vertical member 42, 44 are shown connected to the central gate beam 34 on the attack side of beam 34 proximate to the buttress end 36 and the latch end 38, respectively. The gate frame 40 may further include vertical members 46 spaced apart along the span of the gate frame 40 and connected on their ends to the top and bottom horizontal members 41, 43. The gate frame 40 is a structural frame constructed for example with steel tubing. In some embodiments, the horizontal members 41, 43 and the vertical members 42, 44, 46 are constructed of 3 inch by 4 inch, 11 gauge steel tubing.

Figure 4:
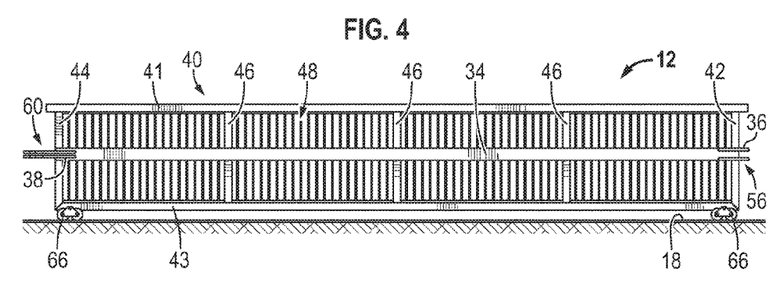
FIG. 4 is an elevation view of a sliding barrier portion of an anti-ram sliding crash gate according to one or more aspects of the disclosure.
Figure 5:
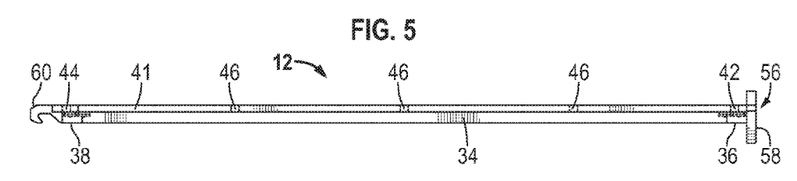
FIG. 5 is a plan view of a sliding barrier portion of an anti-ram sliding crash gate according to one or more aspects of the disclosure.
Figure 6:
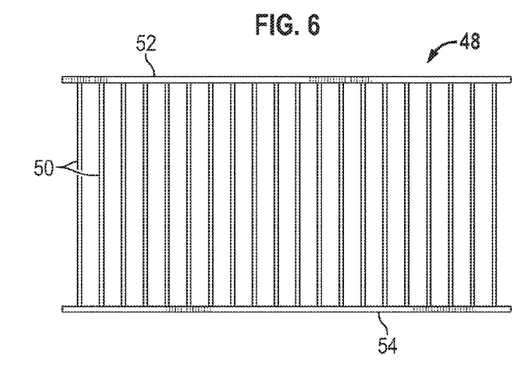
FIG. 6 is an elevation view of a panel of a sliding barrier of an anti-ram sliding crash gate according to one or more aspects of the disclosure.

In some embodiments, the gate frame 40 includes a panel 48, or panels 48, shown in isolation in FIG. 6. The illustrated panels 48 are formed of spaced apart vertical pickets 50 connected to top and bottom rails 52, 54, which are connected with the frame 40, for example between adjacent vertical members 42, 44, and 46, as illustrated in FIG. 4. For example, the vertical pickets 50 are constructed of about 0.5 inch metal pickets spaced apart about four inches on center. In accordance to an embodiment the panels 48 extend about four feet vertically between the top and bottom horizontal members 41, 43 and about seven feet horizontally between adjacent vertical pickets 42, 46, and 44 when configured in a gate frame 40 that extends about thirty feet horizontally for example for a twenty-eight foot roadway.

Figure 7:
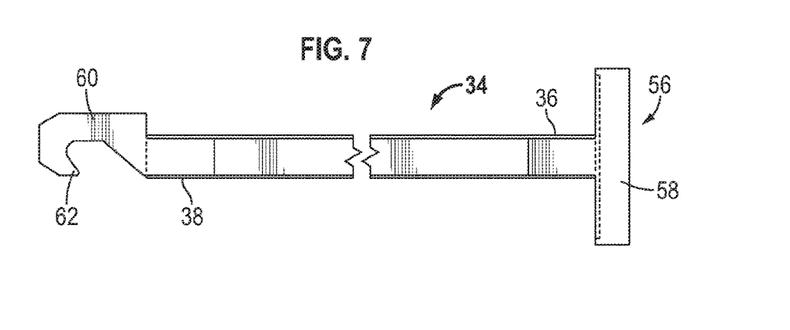
FIG. 7 is a top view of a center gate beam of a sliding barrier of an anti-ram sliding crash gate according to one or more aspects of the disclosure.
Figure 8:
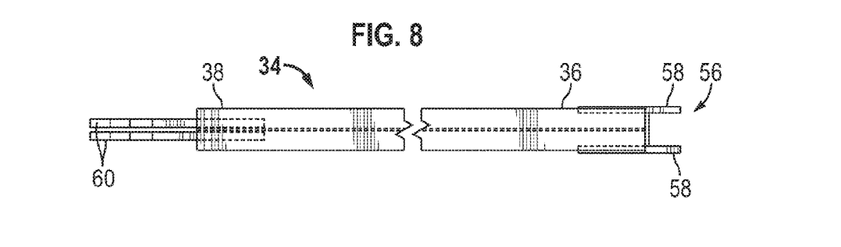
FIG. 8 is a front view of a center gate beam of a sliding barrier of an anti-ram sliding crash gate according to one or more aspects of the disclosure.

FIGS. 7 and 8, described with additional reference in particular to FIGS. 1-5, illustrate an example of a center gate beam 34. A stop mechanism 56, for example a metal plate, is connected, e.g., welded, to the gate beam 34 at the buttress end 36. In the illustrated example, the stop mechanism comprises two spaced apart stop plates 58, for example T-shaped to contact the buttress post assembly 14 (i.e., the T-shaped end is larger than the barrier passage 94) when the barrier 12 is in the closed position (see, e.g., FIG. 2). In accordance to at least one embodiment, the stop plates 58 are constructed of a one-inch steel plate. A latch 60 is connected at the latch end 38 of the gate beam 34 and includes a first latch member 62 to operationally connect with a second latch member 64 at the latch post assembly 16 (see, e.g. FIG. 1). In the non-limiting examples, the first latch element comprises a hook and the second latch element is a pin. In the example of FIG. 8, the latch 60 is formed of two metal plates that are spaced apart and connected to the beam 34.

Figure 9:
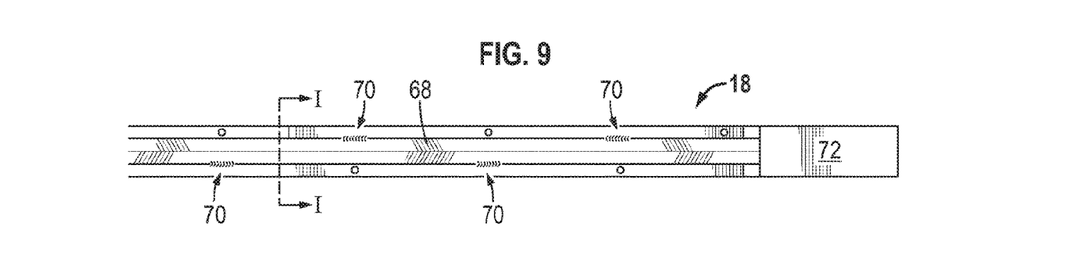
FIG. 9 is a plan view of a portion of a track or rail of an anti-ram sliding crash gate according to one or more aspects of the disclosure.
Figure 10:
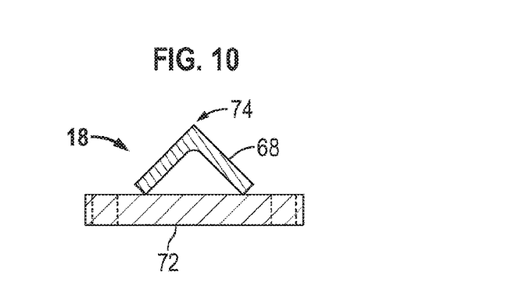
FIG. 10 is a sectional view of the rail or track along the line I-I of FIG. 9.

Referring back to FIGS. 2-4 the barrier 12 may include rollers 66 (i.e., wheels) along the bottom side to move the barrier along the rail 18. FIGS. 9 and 10 illustrate an example of rails or track 18 in accordance to an aspect of the disclosure. For example, the rail 18 may include angle iron 68 connected, for example by welds 70, to a base plate 72 to form a peak 74, which can be disposed in the groove of wheels 66.

Figure 11:
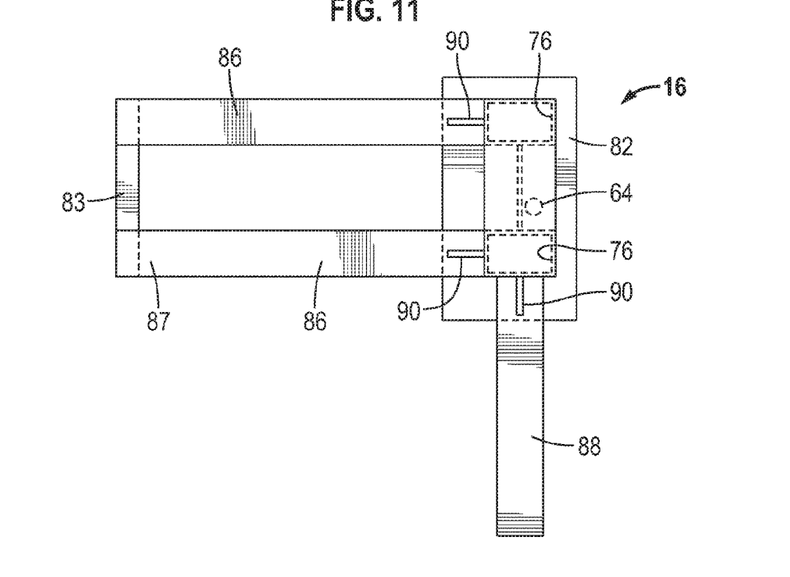
FIG. 11 is a plan view of a latch post assembly of an anti-ram sliding crash gate according to one or more aspects of the disclosure.
Figure 12:
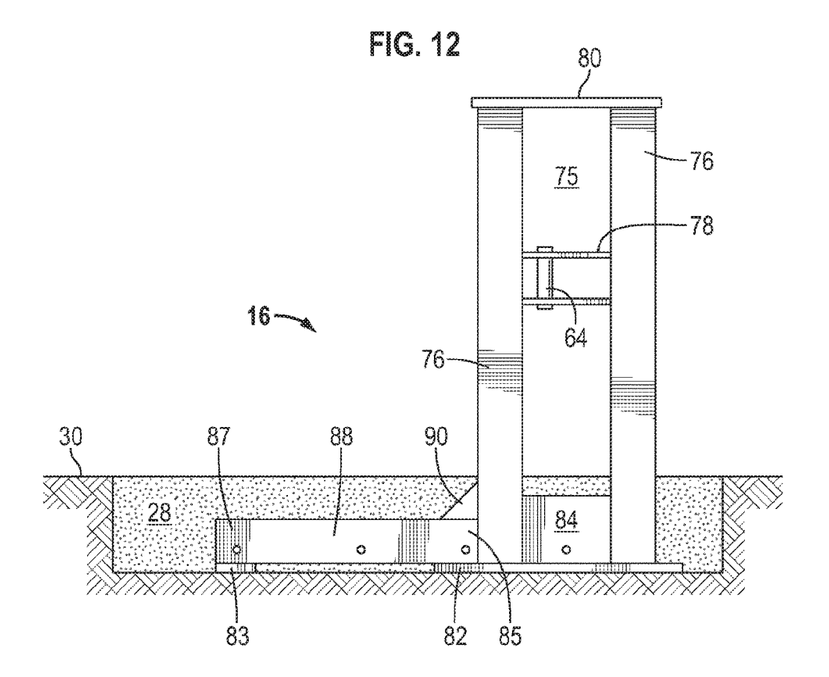
FIG. 12 is an elevation view of a latch post assembly of an anti-ram sliding crash gate according to one or more aspects of the disclosure.
Figure 13:
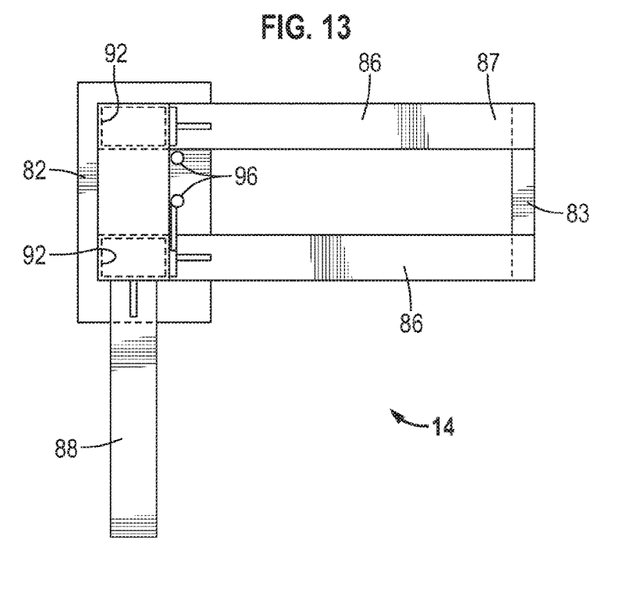
FIG. 13 is a plan view of a buttress post assembly of an anti-ram sliding crash gate according to one or more aspects of the disclosure.
Figure 14:
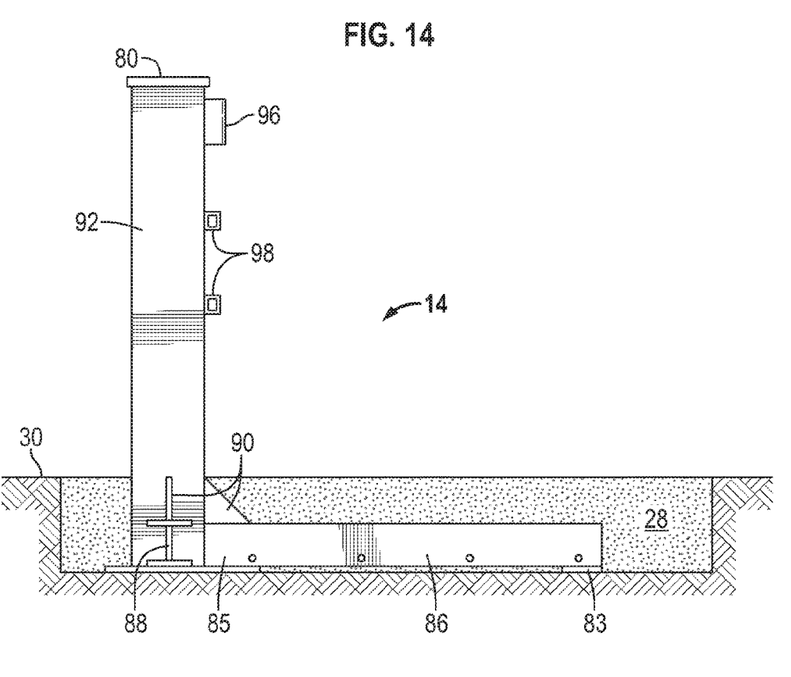
FIG. 14 is an elevation view of a buttress post assembly of an anti-ram sliding crash gate according to one or more aspects of the disclosure.
Figure 15:
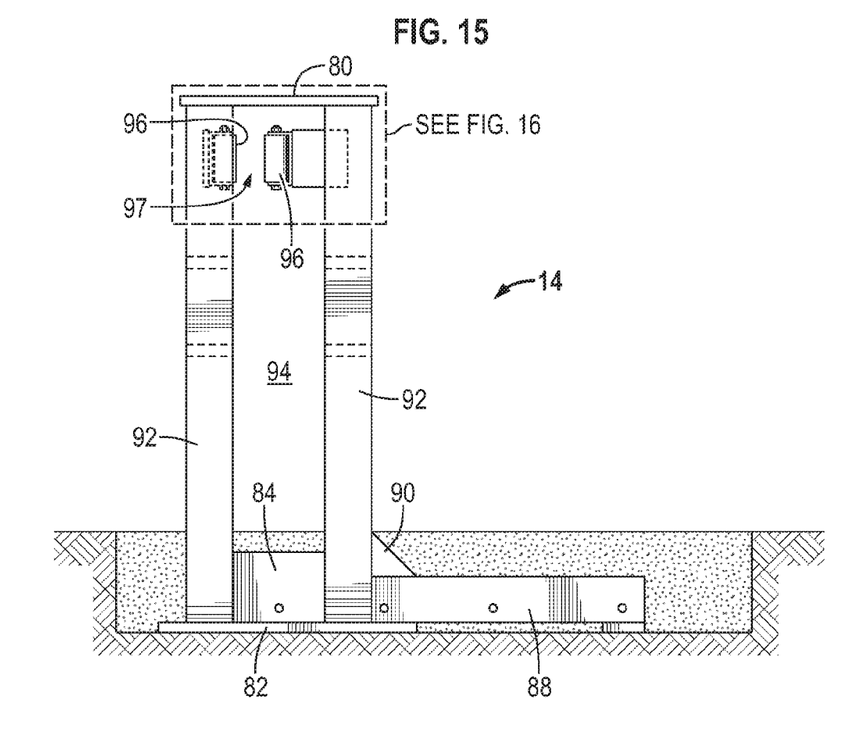
FIG. 15 is a side elevation view of a buttress post assembly of an anti-ram sliding crash gate according to one or more aspects of the disclosure.
Figure 16:
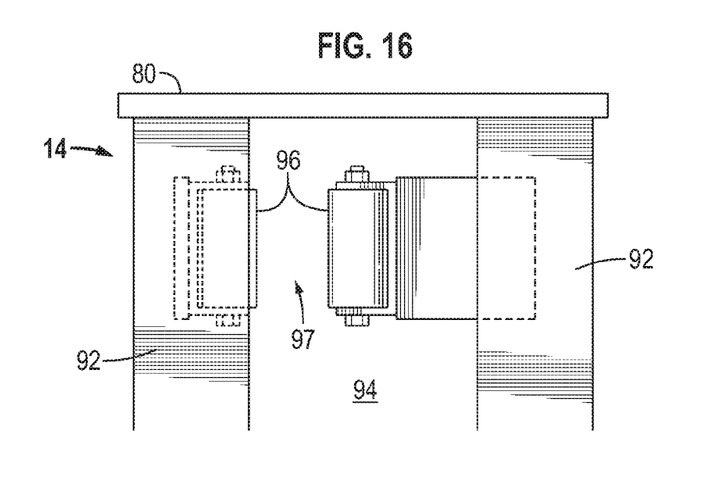
FIG. 16 is an exploded view of a roller section of the buttress post assembly of FIG. 15.

FIGS. 11 and 12 illustrate an example of a latch post assembly 16 according to aspects of the disclosure described with reference to FIGS. 1-6. The latch post assembly 16 includes a pair of vertical latch posts 76 that are spaced apart to form a gap 75 into which at least the first latch member 62, connected to the latch end 38 of the barrier 12 and gate beam 34, can be disposed to connect with the second latch member 64 of the latch post assembly 16. In the illustrated example, the second latch member 64 is a pin (e.g., metal rod) that is connected to the latch posts by strut members 78.

Latch posts 76 are connected to one another for example at the top ends with a cap plate 80 and proximate the bottom ends by base plate 82 and gusset plate 84. A longitudinal leg 86 extends outward from the bottom of each latch post 76 in a direction parallel to the barrier 12 (see, e.g., FIGS. 1 and 2), which is referred to as the longitudinal direction. In the illustrated examples the longitudinal leg 86 extends outward in the direction away from the roadway. The pair of longitudinal legs 86 may be connected at their first ends 85 to the respective latch posts 76 and base plate 82 and connected together proximate to their second ends 87 by a spacer base plate 83. A lateral ground leg 88 is connected at its first end proximate the bottom end of the latch post 76 on the protected side and extends substantially perpendicular to the barrier (longitudinal direction) and toward the protected side. Each of the legs 86 and 88 may further be supported by a brace plate 90 connected between the first end and the respective latch post 76. In accordance to a non-limiting example, the latch posts 76 are constructed of a 12 by 8 inch by 0.5 inch thick steel tubing, the legs 86 and 88 are 8 inch×31 pound/foot wide flange beams (W8×31), and the second latch member 64 is a 2.5 inch diameter steel rod connected to the latch posts with 1-inch steel plates 78.

FIGS. 13 to 16 illustrate an example of a buttress post assembly 14 according to aspects of the disclosure and described with additional reference to FIGS. 1-6. The buttress post assembly 14 includes a pair of vertical buttress posts 92 that are spaced apart to form a passage 94 in which the barrier 12 is disposed. A pair of rollers 96 are connected with the buttress post assembly 14 to provide a pathway 97 between the rollers in which the barrier 12 is positioned. The pathway 97 is sized proximate to the width of the barrier 12 to provide structural strength and support to the sliding barrier.

A pair of vertically spaced apart stops 98 are located on the opposite side of the buttress posts 92 from the roadway for disposing the stop plates 58 on the gate beam 34 when the barrier 12 is in the closed position, see e.g., FIG. 2. In an embodiment the stops 98 are constructed of 2 inch by 2 inch steel bar.

The buttress posts 92 are connected to one another for example at the top ends with a cap plate 80 and proximate the bottom ends by base plate 82 and gusset plate 84. A longitudinal leg 86 extends horizontally outward from the bottom of each buttress post 92 in a direction parallel to the barrier 12 (see, e.g., FIGS. 1 and 2). In the illustrated examples, the longitudinal leg 86 extends outward in the direction away from the roadway. The pair of longitudinal legs 86 may be connected at their first ends 85 to the respective buttress posts 92 and base plate 82 and connected together proximate to their second ends 87 by a spacer base plate 83. A lateral leg 88 is connected at its first end proximate the bottom end of the protected side 24 buttress post and extends substantially perpendicular to the gate and toward the protected side. Each of the ground support legs 86 and 88 may further be supported by a brace plate 90 that is connected between the first end and the respective buttress post 92. In accordance to a non-limiting example, the buttress posts 92 are constructed of a 12 by 8 inch by 0.5 inch thick steel tubing, the legs 86 and 88 are W8×31 beams.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a," "an" and other singular terms are intended to include the plural forms thereof unless specifically excluded.

What is claimed is:

1. A crash gate assembly to guard against motor vehicles crossing in the direction from an attack side to a protected side, comprising:
    a buttress post assembly secured in a ground, the buttress post assembly including two buttress posts forming a barrier passage;
    a latch post assembly secured in the ground on an opposite side of a roadway from the buttress post assembly, the latch post assembly comprising two latch posts forming a latch gap;
    a pair of vertically spaced apart struts extending across the latch gap and secured to the two latch posts;
    a vertical pin positioned in the latch gap and extending between the pair of vertically spaced apart struts; and
    a barrier including a horizontal gate beam disposed in the barrier passage and extending from a buttress end to a latch end, the latch end comprising a hook open toward the protected side, the barrier slidingly positioned in a closed position with the barrier extending across the roadway and the latch end disposed in the latch gap between the vertically spaced apart struts.

2. The crash gate assembly of claim 1, wherein:
    the buttress post assembly comprises a lateral leg located below the ground and extending substantially perpendicular to the barrier; and
    the latch post assembly comprises a lateral leg located below the ground and extending substantially perpendicular to the barrier.

3. The crash gate assembly of claim 1, wherein:
    the buttress post assembly comprises a lateral leg located below the ground and extending substantially perpendicular to the barrier and away from the attack side, and a longitudinal leg located below the ground and extending substantially parallel to the barrier and away from the roadway; and
    the latch post assembly comprises a lateral leg located below ground and extending substantially perpendicular to the barrier and away from the attack side, and a longitudinal leg located below the ground and extending substantially parallel to the barrier and away from the roadway.

4. The crash gate assembly of claim 1, wherein the barrier comprises a rectangular frame connected to the gate beam.

5. The crash gate assembly of claim 1, wherein the barrier comprises a rectangular frame connected to the gate beam; and
    the buttress end is T-shaped and extends outside the rectangular frame, the T-shaped buttress end being larger than the barrier passage.

6. The crash gate assembly of claim 1, wherein:
    the barrier comprises a rectangular frame connected to the horizontal gate beam;
    the buttress end is T-shaped and extends outside the rectangular frame, the T-shaped buttress end having a lateral width greater than a lateral width of the barrier passage;
    the buttress post assembly comprises a lateral leg located below the ground and extending substantially perpendicular to the barrier and away from the attack side, and a longitudinal leg located below the ground and extending substantially parallel to the barrier and away from the roadway;

the latch post assembly comprises a lateral leg located below ground and extending substantially perpendicular to the barrier and in a direction away from the attack side, and a longitudinal leg located below the ground and extending substantially parallel to the barrier and away from the roadway;

the two buttress posts are interconnected proximate their top ends and proximate their bottom ends; and the two latch posts are interconnected proximate their top ends and proximate their bottom ends.

7. The crash gate assembly of claim 1, wherein the buttress end is positioned on the opposite side of the two buttress posts from the raodway and the buttress end has a lateral width greater than a lateral width of the barrier passage.

8. The crash gate assembly of claim 1, wherein the crash gate assembly is crash certified ASTM F2656.

9. The crash gate assembly of claim 8, wherein the buttress end is positioned on the opposite side of the two buttress posts from the roadway and d the buttress end has a lateral width greater than a lateral width of the barrier passage.

10. The crash gate assembly of claim 1, wherein the crash gate assembly is crash certified ASTM F2656 M50-P2.

11. The crash gate assembly of claim 10, wherein the buttress end is positioned on the opposite side of the two buttress posts from the roadway and the buttress end has a lateral width greater than a lateral width of the barrier passage.

12. The crash gate assembly of claim 1, wherein the vertical pin is positioned outside of the hook when the barrier is in the closed position.

13. The crash gate assembly of claim 12, wherein the crash gate assembly is crash certified ASTM F2656.

14. The crash gate assembly of claim 12, wherein the crash gate assembly is crash certified ASTM F2656 M50-P2.

15. A crash gate assembly for arresting an impacting motor vehicle of substantial mass traveling in a direction from an attack side to a protected side within a selected distance;

the crash gate assembly comprising:

a buttress post assembly secured in a ground comprising two buttress posts forming a barrier passage;

a latch post assembly secured in the ground on an opposite side of a roadway from the buttress post assembly, the latch post assembly comprising two latch posts forming a latch gap;

a pair of vertically spaced apart struts extending across the latch gap and secured to the two latch posts;

a vertical pin positioned in the latch gap and extending between the pair of vertically spaced apart struts; and a barrier comprising a horizontal gate beam disposed in the barrier passage and extending from a buttress end to a latch end, the buttress end having a lateral width greater than a lateral width of the barrier passage, and the latch end comprising a hook open toward the protected side, wherein the barrier is slidingly positioned in a closed position with the barrier extending across the roadway with the buttress end positioned on the opposite side of the two buttress posts from the roadway and with the latch end disposed in the latch gap between the vertically spaced apart struts on the attack side relative to the vertical pin.

16. The crash gate assembly of claim 15, wherein the selected distance is approximately twenty-three feet or less for a motor vehicle having a mass of approximately 15,000 pounds and traveling at a speed of about 47 miles per hour or greater.

17. The crash gate assembly of claim 15, wherein the selected distance is approximately twenty-three feet or less for a motor vehicle having a mass of approximately 15,000 pounds and traveling at a speed of less than 47 miles per hour.

18. The crash gate assembly of claim 15, wherein the vertical pin is positioned outside of the hook when the barrier is in the closed position.

19. The crash gate assembly of claim 18, wherein the selected distance is approximately twenty-three feet or less for a motor vehicle having a mass of approximately 15,000 pounds and traveling at a speed of about 47 miles per hour or greater.

20. The crash gate assembly of claim 18, wherein the selected distance is approximately twenty-three feet or less for a motor vehicle having a mass of approximately 15,000 pounds and traveling at a speed of less than 47 miles per hour.

* * * * *